US00PP31006P3

(12) United States Plant Patent

Marsh et al.

(10) Patent No.: US PP31,006 P3
(45) Date of Patent: Nov. 5, 2019

(54) KIWIFRUIT PLANT NAMED 'ZES007'

(50) Latin Name: ***Actinidia deliciosa* C.F. Liang & A.R. Ferguson**
Varietal Denomination: ZES007

(71) Applicant: Zespri Group Limited, Mount Maunganui (NZ)

(72) Inventors: Hinga Marsh, Papamoa (NZ); Elizabeth Popowski, Te Puke (NZ)

( * ) Notice: Subject to any disclaimer, the term of this patent is extended or adjusted under 35 U.S.C. 154(b) by 0 days.

(21) Appl. No.: 15/731,170

(22) Filed: Apr. 28, 2017

(65) Prior Publication Data

US 2018/0317355 P1 Nov. 1, 2018

(51) Int. Cl.

| | |
|---|---|
| ***A01H 5/08*** | (2018.01) |
| ***A01H 6/00*** | (2018.01) |
| ***A01H 6/36*** | (2018.01) |

(52) U.S. Cl.
USPC ..... Plt./156
CPC ..... *A01H 6/00* (2018.05); *A01H 5/08* (2013.01); *A01H 6/36* (2018.05)

(58) Field of Classification Search
USPC ..... Plt./156
See application file for complete search history.

(56) References Cited

PUBLICATIONS

Plant Breeders' Rights to a Kiwiplant named 'ZES007', JP PBR 30639, published Sep. 29, 2016.*
Plant Breeders' Rights to Kiwiplant named 'ZES007', QZ PBR 20161215, May 18, 2016.*
Plant Breeders' Rights to Kiwiplant named 'ZES007', AU PBR 2016119, Jun. 1, 2016.*

* cited by examiner

*Primary Examiner* — Anne Marie Grunberg

(57) ABSTRACT

A new, distinct, and stable *Actinidia deliciosa* variety of plant is disclosed. The plant variety results from the selection among a population of seedlings derived from crossing the kiwifruit selections known as T99.40-02-10c (formerly referenced as 40-02-10c.99, unpatented) and T92.40-08-14e (formerly referenced as 40-80-14e.92, unpatented). The variety of plant is characterized by a medium time of harvest, a medium time of peak flowering (i.e., 70% flower burst), prolific flower production, and fruit that is high in weight and has a sweet, tropical flavor. The new *Actinidia deliciosa* variety of plant has been named 'ZES007'.

4 Drawing Sheets

Latin name of the genus and species of the plant claimed: *Actinidia deliciosa* C. F. Liang & A. R. Ferguson.

Variety denomination: 'ZES007'.

BACKGROUND AND SUMMARY OF THE DISCLOSURE

The disclosure relates to the discovery and asexual propagation of a new and distinct variety of kiwifruit, *Actinidia deliciosa* C. F. Liang & A. R. Ferguson 'ZES007', as herein described and illustrated. The new kiwifruit variety 'ZES007' was selected from a population of seedlings derived from crossing two unpatented kiwifruit selections: *A. deliciosa* female T99.40-02-10c (formerly referenced as 40-0210c.99) x *A. deliciosa* male T92.40-08-14e (formerly referenced as 40-80-14e.92) by controlled pollination and as part of a large breeding program. The cross was made in 2002 at Te Puke, Bay of Plenty, New Zealand. The variety was selected as T03.52-19-12f and has been named 'ZES007'. It was selected for its early flowering and maturation time to harvest and is distinguishable from its parent in that it has a higher fruit soluble solids content and a higher fruit percent dry matter than its maternal parent.

BRIEF DESCRIPTION OF THE DRAWINGS

The accompanying photographs show typical specimens in full color of the fruit, flowers, and leaves of the new variety 'ZES007', plants observed were between 4 years and 6 years from grafting. The colors as depicted are as nearly true as is reasonably possible in a color representation of this type. Colors may vary depending upon growing conditions under different climate, soil, and cultivation conditions. Fruit skin color may also vary depending upon extent of exposure to direct sunlight.

The file of this patent contains at least one drawing executed in color. Copies of this patent with color drawing(s) will be provided by the Patent and Trademark Office upon request and payment of the necessary fee.

Figure 1:
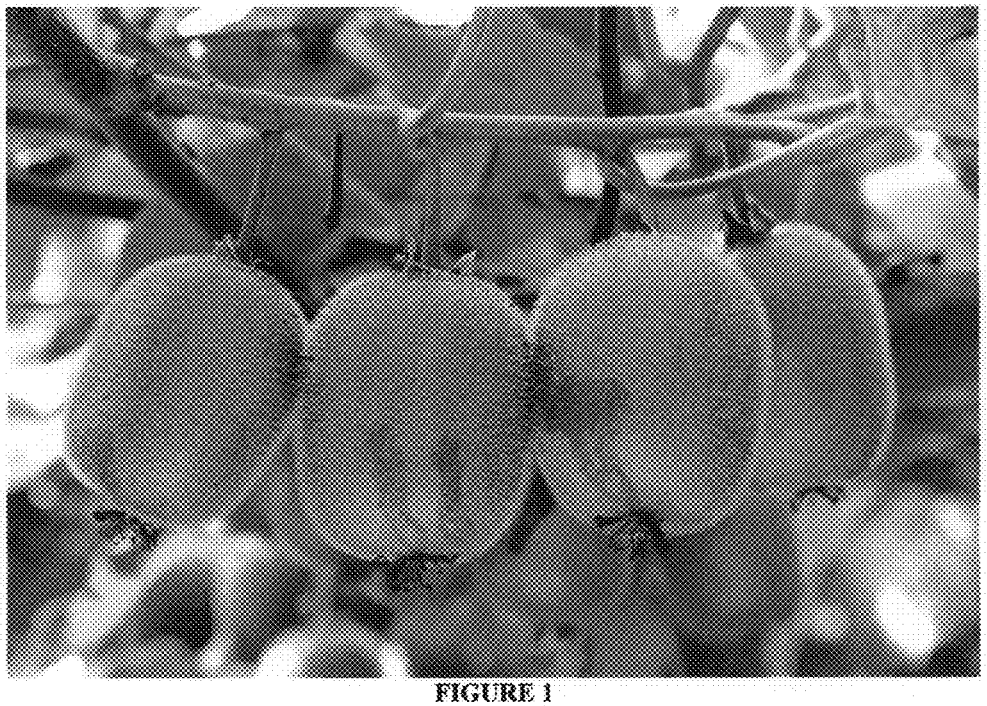
Figure 2:
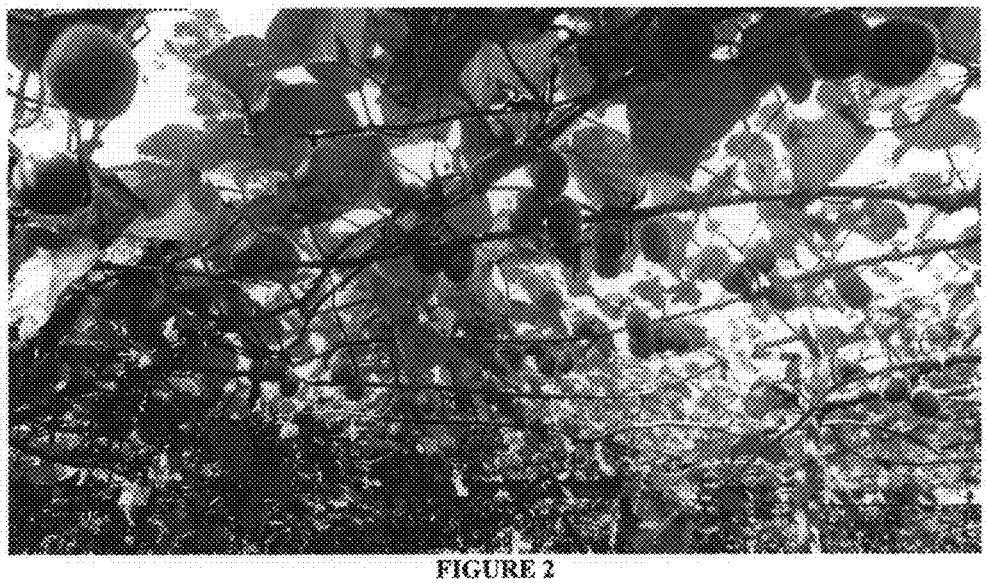
Figure 3:
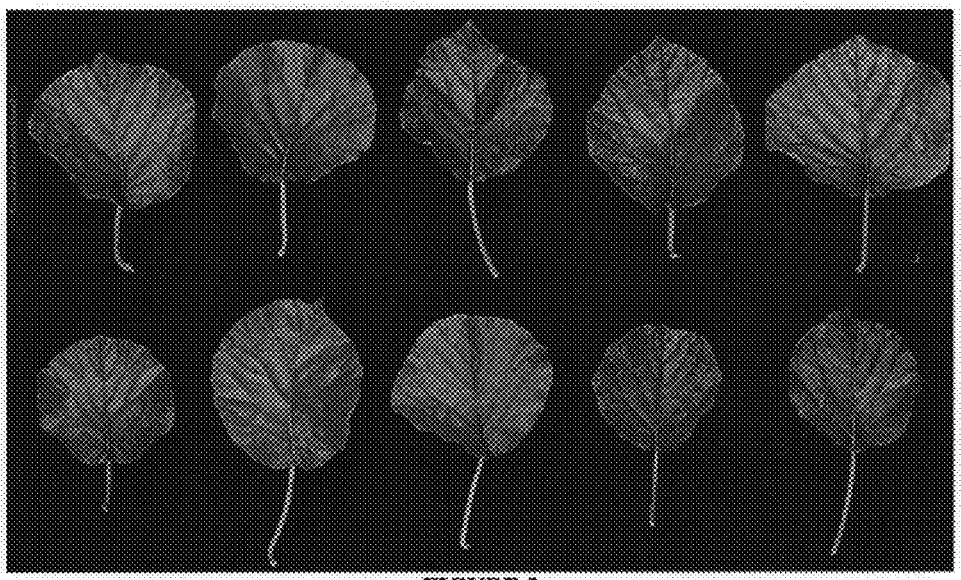
Figure 4:
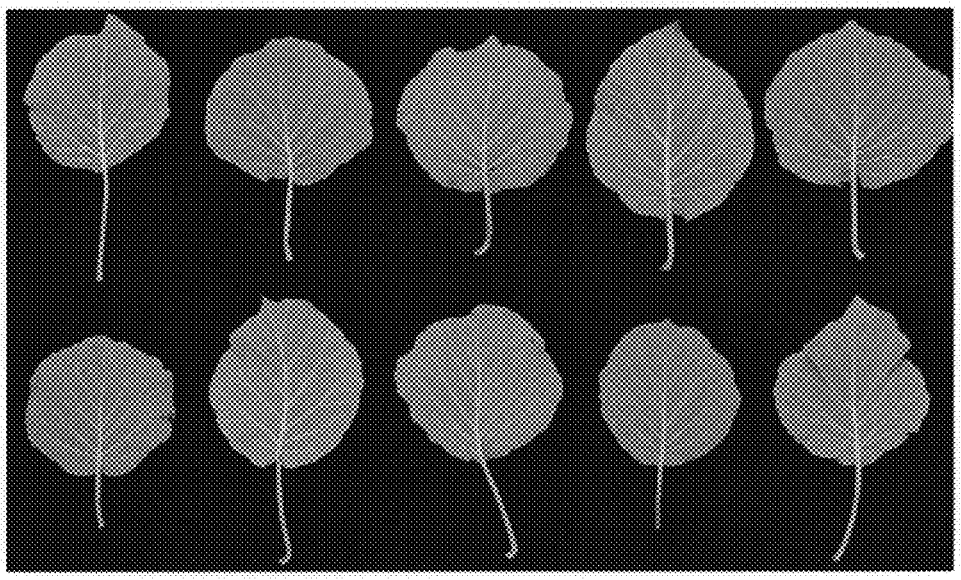
Figure 5:
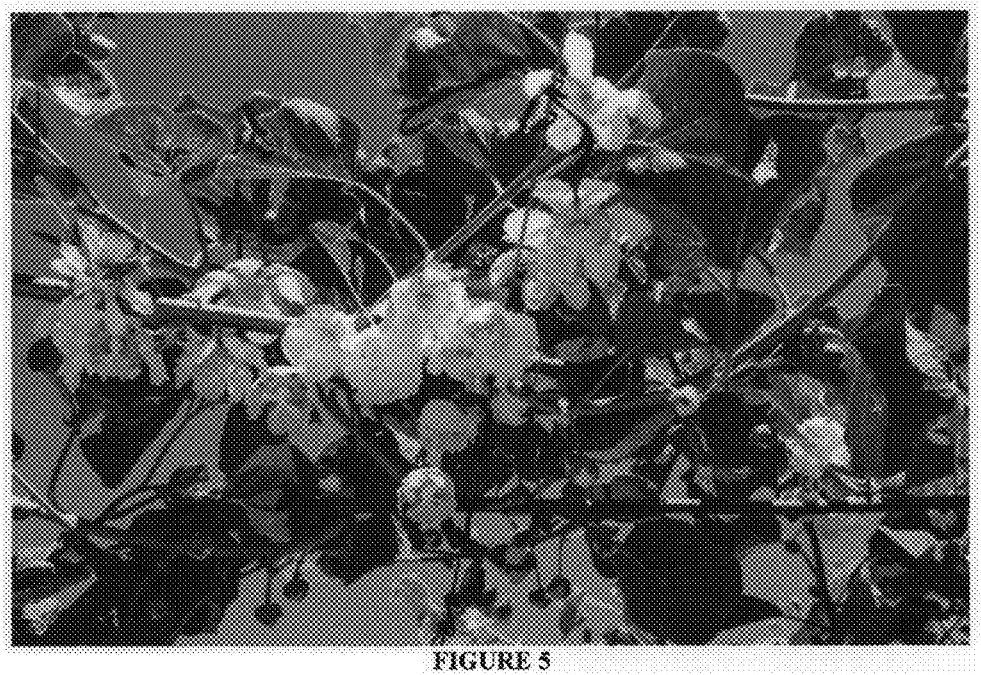
Figure 6:
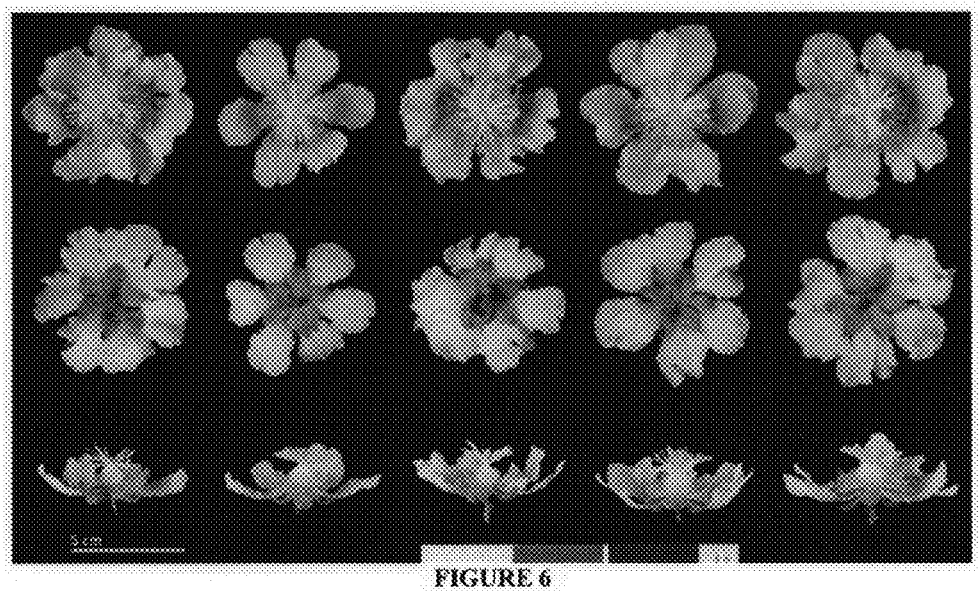
Figure 7:
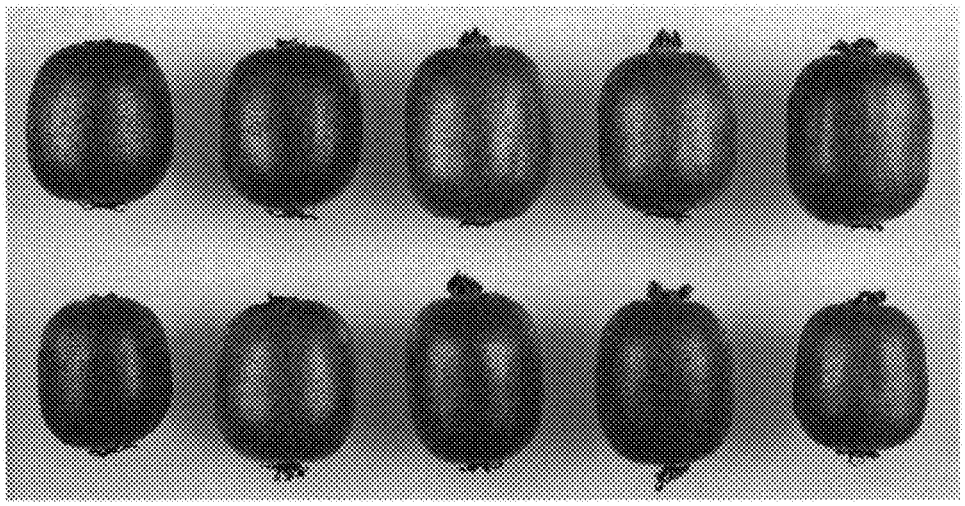
Figure 8:
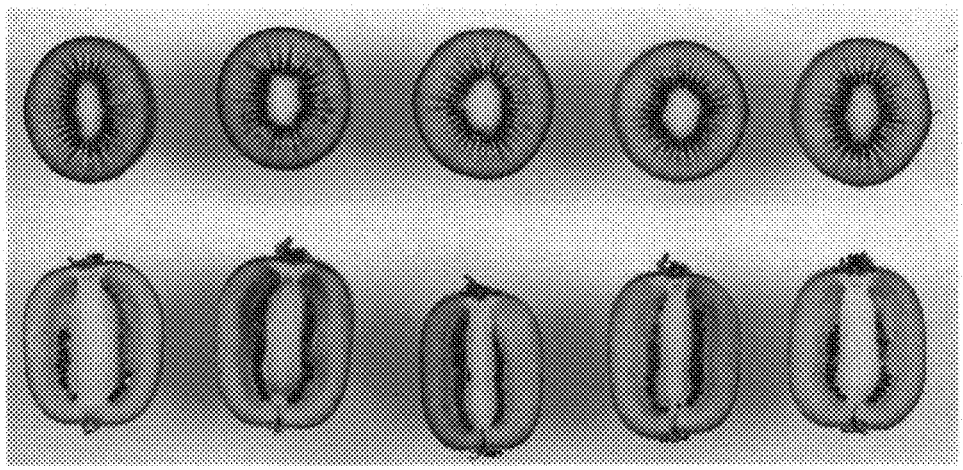

Some embodiments of the disclosure may be understood by referring, in part, to the present disclosure and the accompanying photographs, wherein:

FIG. 1 illustrates a typical fruit (on the vine) of the disclosed variety 'ZES007' according to a specific example embodiment of the disclosure;

FIG. 2 illustrates typical shoots of the disclosed variety 'ZES007' according to a specific example embodiment of the disclosure;

FIG. 3 illustrates the adaxial (top) surface of typical mature leaves of the disclosed variety 'ZES007' according to a specific example embodiment of the disclosure;

FIG. 4 illustrates the abaxial (bottom) surface of typical mature leaves of the disclosed variety 'ZES007' according to a specific example embodiment of the disclosure;

FIG. 5 illustrates typical flowers (on the vine) of the disclosed variety 'ZES007' according to a specific example embodiment of the disclosure;

FIG. 6 illustrates typical flowers (in the studio) of the disclosed variety 'ZES007' according to a specific example embodiment of the disclosure;

FIG. 7 illustrates a typical fruit (in the studio) of the disclosed variety 'ZES007' according to a specific example embodiment of the disclosure; and FIG. 8 illustrates a typical fruit of the disclosed variety 'ZES007' in cross-section (top) and longitudinal-section (bottom) according to a specific example embodiment of the disclosure.

DETAILED DESCRIPTION

The following is a detailed description of the new plant variety. The specimens described were bred, grown, and asexually reproduced and maintained at The New Zealand Institute for Plant and Food Research Limited located at Kerikeri, Northland, New Zealand. Vines of 'ZES007' were grafted onto existing *A. deliciosa* rootstock and grown in replicated plots alongside comparison varieties including Hort16A and Hayward. Comparable observations were made of specimens grown in other growing regions of New Zealand including Bay of Plenty, Northland, Gisborne, and Nelson.

All varieties were managed under standard orchard practice. This included growing the plants on a standard pergola structure at a height of 1.8 m, and allowing each plant to canopy an area of approximately 15 $m^2$. The plants were one year in age when considered mature and first described. The varieties were analyzed and described for six years thereafter. Except where otherwise noted, measurements of each characteristic were obtained from six randomly selected plants.

Horticultural terminology is used in accordance with UPOV guidelines for kiwi varieties. All dimensions are in millimeters and all weights are in grams (unless otherwise stated). Certain characteristics of this variety, such as growth and color, may change with changing environmental conditions (e.g., light, temperature, moisture), nutrient availability, rootstocks, or other factors. Color descriptions and other terminology are used in accordance with their ordinary dictionary descriptions, unless the context clearly indicates otherwise. Color names beginning with a capital letter designate values based upon The R.H.S. Colour Chart published by The Royal Horticultural Society, London, England.

Botanical Description of the Plant

The new variety, 'ZES007' is described in detail below. Traditional fruit breeding methodology was used to develop new kiwifruit varieties as part of a large breeding program. In 2002, 'ZES007' was bred by hybridization through the controlled pollination of female plants of the variety T99.40-02-10c (formerly referenced as 40-02-10c.99) with male pollen of the variety T92.40-08-14e (formerly referenced as 40-80-14e.92). The seedling first bloomed in 2005. In 2007, seedlings (progeny plants) were selected based on project criteria for characteristics such as productivity, fruit size, fruit shape, flesh color, taste, and cold storage characteristics. In 2008, the selected progeny were asexually propagated and grafted onto rootstock (e.g., 'Bruno') for further evaluation and selection (replicated clonal trials). The replicated clonal trials were evaluated between 2008 and 2011 for uniformity and stability.

Male pollen parent T92.40-08-14e was bred by The New Zealand Institute for Plant and Food Research. The male pollen parent is distinguishable from 'ZES007' at least in that it does not bear fruit.

Female parent T99.40-02-10c was also bred by The New Zealand Institute for Plant and Food Research. The female parent is distinguishable from 'ZES007' at least in that it has lower fruit soluble solids content and a lower fruit percent dry matter.

The variety 'ZES007' is maintained by vegetative propagation through cutting, propagation, and grafting. Suitable male pollinizers for the candidate variety include *Actinidia deliciosa* M36 and *Actinidia deliciosa* M43. Other potential pollinizers include 'King', 'Chiefton', and 'M56', however flower synchronization is not ideal using these varieties.

Plant and Foliage

The disclosed variety is a female plant (UPOV 1: female) that is hexaploid (UPOV 6: haxaploid) and lacks self-setting (UPOV 1: absent). It expresses a quiet spreading habit producing a high proportion of self-terminating shoots.

Many young shoots of 'ZES007' have bright yellow-green coloration (RHS 144A) and exhibit dense tomentose hairs (e.g., comparable to 'Hayward', 'Koryoku') (UPOV 7: dense). The anthocyanin (red) coloration on the growing tips of the young shoots is weak to absent (UPOV 1: absent or UPOV 2: weak).

Dormant one-year-old stems (FIG. 1, FIG. 2) of 'ZES007' have orange-brown (RHS 166C-166D) coloring on the upper side. On average, dormant one-year old stems have 5.6 lenticels per $cm^2$ (UPOV 5: medium), with the lenticels having a light brown color (RHS N99B). One year old stems typically have a medium (UPOV 2: medium) covering of short, soft hairs. The hairs have interveinal coloration of white to pale yellow. On average, mature one-year old shoots of 'ZES007' have a bud cover (UPOV 9: present) with a medium-sized hole (e.g., comparable to 'Hayward') (UPOV 2: medium).

The leaf blade of 'ZES007' is ovate in shape (e.g., comparable to 'Hayward') (UPOV 2: ovate) with an acuminate-shaped leaf tip (FIG. 3, FIG. 4) (e.g., comparable to 'Hayward') (UPOV 2: acuminate). The ratio of length:width of the leaf blade is intermediate (e.g., comparable to 'Hayward') (UPOV 5: intermediate). A typical 'ZES007' leaf blade is RHS N137A green on the upper surface (FIG. 3) and RHS N137B green on the lower surface (FIG. 4), with the basal lobes of the leaves touching each other (e.g., comparable to 'Hort16A') (UPOV 4: touching each other). Typically the leaves are not variegated (UPOV 1: absent). On average, the length of a petiole relative to a mature blade is 0.56 (range 0.42 to 0.86). 'ZES007' petioles of a mature leaf often have strong anthocyanin coloration on the upper side that is dark pink (RHS 185A) in color.

Inflorescence

Characteristics of 'ZES007' inflorescence were calculated based on the results of a 20 flower sample. The inflorescence (FIG. 5) of 'ZES007' is solitary (e.g., comparable to 'Jinkui') (UPOV 1: solitary) with the average number of flowers present in each inflorescence typically being very few (UPOV 1: very few). 'ZES007' flowers typically have an average of 5.7 sepals (range 4 to 8 sepals) (UPOV 3: medium). Flowers of 'ZES007' are, on average, 75.1 mm in diameter (range 65.2 mm to 83.9 mm) with overlapping petals (e.g., comparable to 'Hayward', 'Shinzan') (UPOV 3: overlapping) (FIG. 6). Each flower typically has about 40 styles (range 32 to 53) (UPOV 2: medium), the styles having a semi-erect attitude (UPOV 2: semi-erect). Petals are white in color on the adaxial side (RHS 155D) (UPOV 1: white) with even shading of the main color (UPOV 2: even) and light-green secondary coloration at petal base only. Anthers are yellow in color (e.g., comparable to 'r-Nagano') (UPOV 1: yellow). Anthocyanin (red) coloration of the ovaries in cross-section is absent at mid-bloom.

Fruit

The 'ZES007' plant produces a fruit that is obovate in shape (FIG. 7) (e.g., comparable to 'Monty') (UPOV 6: obovate), with an average length of 65.8 mm (range 61.3 mm to 74 mm) (UPOV 5: medium) and an average width of 58.2 mm (range 52.2 mm to 63 mm) (UPOV 5: medium). 'ZES007' produces fruit with high weight, averaging around 128 g (range 96 g to 157 g) (UPOV 7: high). 'ZES007' fruit has a flat stylar end (e.g., comparable to Hayward) (UPOV 3: flat). The stalk of 'ZES007' fruit is grey-brown to brown (RHS 200C) in color and, on average, is 32.5 mm (range 21 mm to 42.5 mm) in length, with the length of the stalk relative to the length of the fruit being 0.49 (range 0.34 to 0.68). Mature 'ZES007' fruit has grey-brown skin (RHS N199A) with greenish tones that strongly adheres to the flesh of the fruit (UPOV 3: strong).

The fruit of 'ZES007' is hairy (e.g., comparable to 'Hayward') (UPOV 9: present), having a medium density (UPOV 5: medium) of bright brown colored hairs (RHS 165B). The hairs are long (e.g., comparable to 'Hayward', 'Koryoku') and weakly adhere (e.g., comparable to 'Hort16A') to the skin of the 'ZES007' fruit (UPOV 3: weak).

The outer pericarp of 'ZES007' is yellow-green (RHS 145A) in color. The fruit flesh is yellow-green (RHS 145A) in color. The locules of 'ZES007' fruit are yellow-green (RHS 145A) to medium green in color (e.g., comparable to 'Hayward', 'Hortgem Tahi') (UPOV 2: medium green).

The fruit core (FIG. 8) of 'ZES007' is yellow-green in color (RHS 154D) and oblate in shape (e.g., comparable to 'Hort22D').

'ZES007' fruit has sweet and tropical flavors, with an average ripe brix value of 15.4 (range 12.8 to 17.6). On average 'ZES007' has an acidity value of 1.23 (range 1.15 to 1.31). An average 'ZES007' fruit contains approximately 18% soluble solids and approximately 20% dry matter.

Timing of Horticultural Events

'ZES007' plants display a medium timing of vegetative bud burst (e.g., comparable to 'Hayward', 'Shinzan') (UPOV 5: medium). The beginning of flowering time for 'ZES007' plants is medium (e.g., comparable to 'Abbott', 'Kousui') (UPOV 5: medium). The flowering time at which 70% of 'ZES007' flowers have opened is medium (e.g., comparable to 'Rozanko', 'Kimpo', 'Matua'). In the Southern Hemisphere flowering time for 'ZES007' is typically observed from the beginning of November to the end of November.

The timing of fruit maturity for harvest of 'ZES007' plants is medium (e.g., comparable to 'Kousui', 'Tomua') (UPOV 5: medium). Fruit harvest in the Te Puke region of New Zealand typically occurs between the beginning of April to the end of May.

In the Te Puke region of New Zealand 'ZES007' fruit maturation typically occurs from the beginning of May to the beginning of August. 'ZES007' fruit may be ripened using ethylene gas. Fruit may also soften during cold storage and become ripe for eating within 6 to 12 weeks at 1° C.

Cultivation

'ZES007' is maintained as grafted plants in an orchard setting in the Te Puke region of New Zealand by appropriate personnel at the New Zealand Institute for Plant and Food Research. The typical rootstock for 'ZES007' is 'Bruno', however 'ZES007' plants can be grown on the same rootstocks as other standard varieties (e.g., 'Hayward' and 'Hort16'). Rootstocks currently being used in New Zealand include *A. deliciosa* seedlings and rooted cuttings of 'Hayward' or 'Kaimai'.

In the Southern hemisphere, seeding may be performed throughout the month of April. Planting, grafting, and cutting may be performed in the Southern hemisphere from the beginning of July through the end of August. Flowering time in the Southern hemisphere is generally observed between the beginning and end of November. In the Southern hemisphere, harvest time may be practiced from the beginning of April through late May, with the maturation period of the 'ZESY007' fruit being generally observed from the beginning of May to the beginning of August.

Comparison to Parental Varieties

The distinctive characteristics of this new *Actinidia deliciosa* variety, 'ZES007', described above in detail, were observed in the Te Puke region of New Zealand at the New Zealand Institute for Plant and Food Research. Maternal parent variety T99.40-02-10c was grown in another block of the same orchard. Variations noted below between 'ZES007' and the parental varieties are for example purposes only and should not be construed as the only variations between the varieties. Other variations between 'ZES007' and the parental varieties may exist.

The fruit of the maternal parent variety T99.40-02-10c has a lower percentage of soluble solids (approximately 15% soluble solids) when compared to 'ZES007' (approximately 18% soluble solids). Additionally, fruit of the maternal parent variety T99.40-02-10c has a lower percentage of dry matter (approximately 17% dry matter) when compared to 'ZES007' (approximately 20% dry matter). The fruit of 'ZES007' has a sweet, tropical flavor compared to a sour flavor of T99.40-02-10c fruit.

Male parent variety T92.40-08-14e does not bear fruit.

Comparison to Closest Cultivars

The distinctive characteristics of 'ZES007', described above in detail, were observed in the Te Puke region of New Zealand at the New Zealand Institute for Plant and Food Research. Comparison vines of varieties 'ZESH004' and 'Hayward' were grown in another block of the same orchard. Variations noted below between 'ZES007' and the varieties listed below are for example purposes only and should not be construed as the only variations between the varieties. Other variations between 'ZES007' and the noted varieties may exist.

At least, 'ZES007' differs from the variety 'Hayward' in: the fruit shape; the adherence of hairs to fruit skin; the color of outer pericarp of fruit; the color of fruit core; the time of harvest; and the time of peak flowering (i.e., 70% flower burst), as shown below in TABLE 1.

TABLE 1

| | ZES007 | Hayward |
|---|---|---|
| FLOWER | | |
| Flower: production | 4 king flowers per winter bud on one-year old canes | 0.5 king flowers per winter bud on one-year old canes |
| FRUIT (From a 20 fruit sample) | | |
| Fruit: shape | 6: obovate | 3: elliptic |
| Fruit: adherence of hairs to skin | 3: weak | 7: strong |
| Fruit: color of outer pericarp | 4: greenish yellow | 2: medium green |
| Fruit: color of core | yellow-green | 2: greenish white |
| EVENTS | | |
| Time of beginning of flowering | 5: medium | 7: late |
| Time of maturity for harvest (at 10.0% soluble solids content) | 5: medium | 7: late |

At least, 'ZES007' differs from the variety 'ZESH004' in: the stem color on the upper side of shoot; the density of hairs on the stem; the color of lenticels on the stem; the general shape of the leaf blade; the shape of the leaf blade apex; fruit weight; fruit shape; the length of hairs on the skin of the fruit; and the color of the outer pericarp of the fruit, as shown below in TABLE 2.

TABLE 2

| | ZES007 | ZESH004 |
|---|---|---|
| STEM | | |
| Stem: color on upper side of shoot | orange-brown (RHS 166C-166D) | light yellow-brown (RHS 164A-164B) |

TABLE 2-continued

| | ZES007 | ZESH004 |
|---|---|---|
| Stem: density of hairs | 2: medium | 1: absent or sparse |
| Stem: color of lenticels | light brown (RHS N99B) | pale yellow-orange (RHS 192B-192C) |
| LEAF (Mature) | | |
| Leaf blade: general shape | 2: ovate | 3: obovate |
| Leaf blade: shape of apex | 2: acuminate | 7: emarginated |
| FLOWER | | |
| Flower: production | 4 king flowers per winter bud on one-year old canes | 0.7 king flowers per winter bud on one-year old canes |
| FRUIT (From a 20 fruit sample) | | |
| Fruit: weight | 7: high; 128 (range 96-157) | 5: medium; 116 |
| Fruit: shape | 6: obovate | 3: elliptic |
| Fruit: length of hairs | 7: long | 3: short |
| Fruit: color of outer pericarp | 4: greenish yellow | 2: medium green; flesh of fruit are green at harvest (RHS 146C) but will change to a yellow-green color (RHS 154A) at warm temperatures of 20° C. or if left to ripen on the vines. |

The title, abstract, background, and headings are provided in compliance with regulations and/or for the convenience of the reader. They include no admissions as to the scope and content of prior art and no limitations applicable to all disclosed embodiments.

What is claimed is:

1. A new, distinct, and stable kiwifruit plant substantially as herein described and illustrated, characterized by a medium time of harvest, a medium time of peak flowering (i.e., 70% flower burst), prolific flower production, and fruit that is high in weight and has a sweet, tropical flavor.

* * * * *